United States Patent
Sager (10) Patent No.: US 6,315,563 B1
(45) Date of Patent: Nov. 13, 2001

(54) SINGLE-TOOTH ENOSSAL IMPLANT (75) Inventor: David R. Sager, Manhattan, KS (US)

(73) Assignee: IMZ Fertigungs-und Vertriebsgesellschaft für dentale Technologie mbH, Filderstadt (DE)

( * ) Notice: Subject to any disclaimer, the term of this patent is extended or adjusted under 35 U.S.C. 154(b) by 0 days.

(21) Appl. No.: 09/647,967
(22) PCT Filed: Apr. 1, 1999
(86) PCT No.: PCT/DE99/01054
§ 371 Date: Dec. 6, 2000
§ 102(e) Date: Dec. 6, 2000
(87) PCT Pub. No.: WO99/52464
PCT Pub. Date: Oct. 21, 1999

(30) Foreign Application Priority Data

Apr. 8, 1998 (DE) ................................ 198 15 719
Jun. 26, 1998 (DE) ................................ 198 28 461
Jul. 2, 1998 (DE) ................................ 198 29 504

(51) Int. Cl.[7] .................................................. A61C 8/00
(52) U.S. Cl. .......................................... 433/173; 433/169
(58) Field of Search .................................. 433/173, 174, 433/169, 172

(56) References Cited

U.S. PATENT DOCUMENTS

| 4,626,214 | * | 12/1986 | Artal | 433/174 |
| 4,631,031 | * | 12/1986 | Richter | 433/173 |
| 4,993,950 | * | 2/1991 | Mensor, Jr. | 433/173 |
| 5,098,294 | * | 3/1992 | Lee et al. | 433/169 |
| 5,122,059 | * | 6/1992 | Durr et al. | 433/173 |
| 5,195,892 | * | 3/1993 | Gersberg | 433/173 |
| 5,302,126 | * | 4/1994 | Wimmer et al. | 433/173 |
| 5,782,918 | * | 7/1998 | Klardie et al. | 433/173 |
| 5,823,776 | * | 10/1998 | Duerr et al. | 433/173 |
| 5,947,734 | * | 9/1999 | Hanel | 433/173 |
| 6,116,904 | * | 9/2000 | Kirsch et al. | 433/173 |

FOREIGN PATENT DOCUMENTS

| 4405797-C1 | * | 5/1995 | (DE) . |
| 19509118-A1 | * | 9/1996 | (DE) . |
| 19534979-C1 | * | 1/1997 | (DE) . |
| 2695822 | * | 3/1994 | (FR) . |

* cited by examiner

Primary Examiner—John J. Wilson
(74) Attorney, Agent, or Firm—Schiff Hardin & Waite (57) ABSTRACT Given a single tooth implant with a base member and an abutment for a crown, whereby the base member, in sequence from the coronal to the cervical end, comprises a positive lock region with positive lock elements for joining to the abutment and a centering region and the abutment, complementary thereto, comprises a positive lock section and a centering section, the positive lock elements of the positive lock region are arranged offset from the face wall of the base member. The centering region can directly adjoin the positive lock region. According to an advantageous embodiment, a seal ring can be provided between the abutment and the base member.

20 Claims, 6 Drawing Sheets

SINGLE-TOOTH ENOSSAL IMPLANT

BACKGROUND OF THE INVENTION

The invention is directed to an enossal single tooth implant, which has a base member, which is inserted in a bore made in a jawbone and has a blind bore extending inward from one end, and an abutment for a crown or dental prosthesis having a centering collar inserted into the blind bore.

DE 195 34 979 C1 discloses a single tooth implant of this species wherein the positive lock region of the base member directly adjoins the coronal face wall thereof. The positive lock section of the abutment is provided essentially immediately following the shoulder of the abutment. Given this implant, moreover, a guide region with a larger diameter than that of the centering region is provided between the positive lock region and the centering region of the base member.

The single tooth implant of the species has in fact essentially proven itself, but it has turned out to be desirable to enhance the mechanical stability even more and, additionally, to simplify the fabrication.

It has also been shown that bacteria or the like can penetrate between the boundary surfaces of the base member and the abutment over the course of time. The recent desire for an effective "biological seal" between the inside of the implant and the oral cavity or, respectively, the gums has not been taken into account as desired, particularly for patients who are especially sensitive to taste and smell. For this reason, a noticeable taste arises, particularly when removing the abutment after having worn it for a longer time and some patients consider this unpleasant. Despite the precision in the working of the surfaces of the base member as well as of the abutment that is currently possible, there is still the problem of a sometimes inadequate seal between the inside of the implant, i.e. the implant chamber that accepts the cervical regions of the abutment and the abutment screw, and the oral cavity. Said seal is not only important to prevent a penetration of bacteria into the implant chamber from the outside but—insofar as bacteria have penetrated into the implant chamber—also because gram-negative, anaerobic bacteria that, insofar as they penetrate into the oral cavity, can easily lead to periodontal processes especially multiply there under the influence of body heat in the dark, anaerobic chamber atmosphere. Overall, thus, a seal of the implant chamber would be desirable in both directions, both from the inside to the outside and from the outside to the inside; this, however, has not yet been satisfactorily achieved in the known single tooth implant for the reasons discussed above.

DE 195 09 118 discloses a single tooth implant with which a mobility of the implant in the jaw or, respectively, jaw bone similar to a natural tooth is to be achieved. To this end, an elastic ring that lies against appertaining seating surfaces of the abutment for the crown and of the base member is inserted between the abutment and the base member. These seating surfaces are of such a nature that the ring is not covered at the outside by the base member and the abutment, so that the abutment can be displaced in the longitudinal direction of the implant and in the direction toward the oral cavity or away from the oral cavity opposite the elastic force of the ring.

SUMMARY OF THE INVENTION

The invention is therefore based on the object of creating a single tooth implant of the species initially cited that is simpler to fabricate.

According to a further aspect of the invention, a single tooth implant of the species initially described should be created wherein a dependable biological seal between the inside of the implant and its outside is assured.

This object is inventively achieved by an enossal single tooth implant for a tight-fitting dental prosthesis having an essentially cylindrical base member, which has a closed end that is insertable into a bore introduced in a jaw bone and comprises a blind bore open toward its coronal or one end and extending toward the closed end, and an abutment for a crown attachable to the coronal face wall of the base member secured against twisting. At a first end, the abutment has a cervical centering collar insertable into a hollow-cylindrical ring recess provided at the coronal end of the base member, and has a shoulder emplaceable onto the coronal face edge of the base member, which is arranged between the centering collar and a fastening head for the dental prosthesis. The abutment has a preferably through central bore for the acceptance of an abutment screw that preferably penetrates the abutment and can be directly or indirectly introduced into the blind bore of the base member. A connecting device for the twist-secured joining of the abutment to the base member is formed in that a positive lock region of the ring recess comprises at least one base member positive lock element acting in circumferential direction and the centering collar comprises at least one abutment positive lock element complementary to the base member positive lock element or elements. A centering region of the ring recess is arranged farther toward the closed end or cervically than the positive lock region. A circumferential guide surface or surfaces of the positive lock region lying closest to the longitudinal center axis of the ring recess lies or lie on a cylinder surface whose diameter is larger than that of the centering region, the abutment positive lock element or elements is/are provided farther cervically than the shoulder at the cylindrical outside wall of the centering collar in a positive lock section thereof, the circumferential surface or surfaces of the positive lock section lying closest to the longitudinal center axis of the centering collar lies/lie on a cylinder surface whose diameter essentially corresponds to that of the cylinder surface on which the circumferential guide surface or surfaces of the positive lock region lying closest to the longitudinal center axis of the ring recess lies or lie. A cylindrical centering section is arranged farther cervically than the positive lock section, the outside diameter thereof essentially coinciding with the inside diameter of the centering region, this being characterized in that the positive lock region is arranged with cervical spacing from the coronal face edge.

It is provided according to a specific embodiment that the centering region immediately cervically adjoins the positive lock region, and that the centering section immediately cervically adjoins the positive lock section.

This embodiment of the invention is based on the surprising perception that, given facilitation and simplification of the fabrication, one succeeds in improving the mechanical stability of the single tooth implant of the species in that the compulsory guide region of the Prior Art with an inside diameter corresponding to the positive lock region of the base member is omitted and the centering region is directly connected to the positive lock region. The intervention of a guide region with a smooth inside wall whose inside diameter corresponds to that of the positive lock region is thus foregone in the base member, so that the centering region with a reduced inside diameter compared to the positive lock region immediately follows the positive lock region in cervical direction.

The centering region can thereby be provided with an inside thread over its entire longitudinal extent. However, it can also be provided that the inside thread only extends over a part of the axial longitudinal extent of the centering region, whereby this part—for manufacturing reasons—preferably immediately adjoins the positive lock region. In that, in this case, a part of the axial longitudinal extent of the guide region, namely the part lying cervically distal or toward the closed end of the base member from the centering region, comprises a smooth, cylindrical inside wall whose inside diameter, of course, corresponds to that of the inside thread in the other part of the centering region, an enlarged seating surface derives between the centering section of the abutment and the base member, as a result whereof the mechanical stability is further-improved. It should thereby be noted that, of course, the abutment is correspondingly modified compared to the single tooth implant according to DE 195 34 979 C1 in that the centering section at the abutment directly adjoins the positive lock section upon elimination of the guide section provided in the parent patent.

In particular, it can also be provided that the inside thread extends over at least 50% of the axial longitudinal extent of the centering region, particularly over about ⅔ of the axial longitudinal extent of the centering region.

Due to the elimination of the guide region at the base member and of the guide section at the abutment in this embodiment, a step-free placement of the centering section (lengthened compared to DE 195 34 979 C1) derives overall at the inside wall of the centering region of the base member (likewise correspondingly lengthened), as a result whereof stress spikes are avoided and the mechanical stability is enhanced.

It can also be provided that a guide region of the ring recess having an essentially smooth circumferential wall cervically adjoins the positive lock region, the diameter thereof corresponding to that of the cylinder surface on which a circumferential guide surface or surfaces of the positive lock region closest to the longitudinal center axis of the ring recess lies/lie, that the centering region of the ring recess adjoins the guide region farther cervically, this comprising a diameter reduced compared to the guide region, that a cylindrical guide section cervically adjoins the positive lock section, the outside diameter thereof essentially corresponding to the inside diameter of the guide region, and the cylindrical centering section cervically adjoins the guide section.

A further embodiment of the invention provides that the positive lock region is arranged cervically spaced from the coronal face edge, that the face edge merges via a concave, partially toroidal base member sealing surface into the circumferential guide surface or surfaces of the positive lock region, that the positive lock section is arranged cervically spaced from the shoulder, whereby the abutment comprises a cylindrical boundary surface between the coronal end of the positive lock section and the shoulder, the diameter of said boundary surface corresponding to that of the centering collar in its cylindrical positive lock section outside the abutment positive lock element or elements, that the shoulder—essentially directly adjoining the boundary surface—comprises an annular shell-shaped annular channel that forms a partially toroidal abutment sealing surface, that the base member sealing surface and the abutment sealing surface, in interaction with one another, form an essentially toroidal seal chamber for the at least approximately complete acceptance of a seal ring, and that a seal ring composed essentially of elastically deformable material is placed into the seal chamber.

Inventively, the seal ring can be fashioned as O-ring and can be composed of plastic such as silicone or the like.

The material of the seal ring can be bacteriostatically/bacteriocidally fashioned.

It can be provided in view of the dimensions that the axial depth of the annular channel amounts to 0.2 through 0.4 mm and/or the radial width of the annular channel amounts to 0.2 through 0.5 mm and/or the axial spacing of the coronal limitation of the positive lock region from the coronal face edge of the base member amounts to 0.2 through 0.5 mm and/or the axial thickness of the seal ring in its unstressed condition amounts to 0.2 through 0.6 mm and/or the outside diameter of the base member amounts to 2.0 through 7.0 mm in the region of its coronal face edge.

The advantageous embodiment of the invention wherein a seal ring is provided between the abutment and the base member is based on the surprising perception that it is possible to assure a dependable biological seal between the inside of the implant and the outside thereof and, for example, to preclude annoying odors, etc., to the farthest-reaching extent, to thus make the single tooth implant more "pleasant" for patients who are especially sensitive to odors, in that, by foregoing the direct joining of the positive lock elements of the base member to the face edge thereof while simultaneously foregoing the direct joining of the positive lock elements of the abutment to the shoulder thereof intended for placement onto the face edge of the base member, an essentially toroidal, i.e. cross-sectionally essentially circular, seal chamber is created by providing partially toroidal sealing surfaces adjoining, on the one hand, the face edge of the base member and, on the other hand, in the seating surface of the shoulder of the abutment proceeding perpendicularly to the longitudinal center axis of the abutment, a seal ring, preferably an O-ring, composed of silicone or some other elastic material being placed in said seal chamber. This O-ring assumes no guide function whatsoever but, given suitable play between the base member and the abutment, can even serve as shock absorber between these components parts both in axial as well as lateral direction. It is thereby critical to the invention that the base member sealing surface does not, for instance, merely represent a bevel in the form of a partially toroidal surface but is fashioned partially circular-concave in radial section in order to thus be able to optimally accept the seal ring in the seal chamber.

In that the partially toroidal sealing surface characteristic of the inventive single tooth implant is provided adjoining the coronal face edge of the base member, moreover, stress spikes are very advantageously avoided that, given corresponding stressing, could otherwise occur close to the upper face edge in, on the one hand, the material of the abutment but, on the other hand, also in that between the coronal face edge surface of the base member and the adjoining part of the ring recess of the base member.

Further features and advantages of the invention derive from the following description wherein exemplary embodiments are explained in detail on the basis of schematic drawings.

DESCRIPTION OF THE PREFERRED EMBODIMENTS

Figure 1:
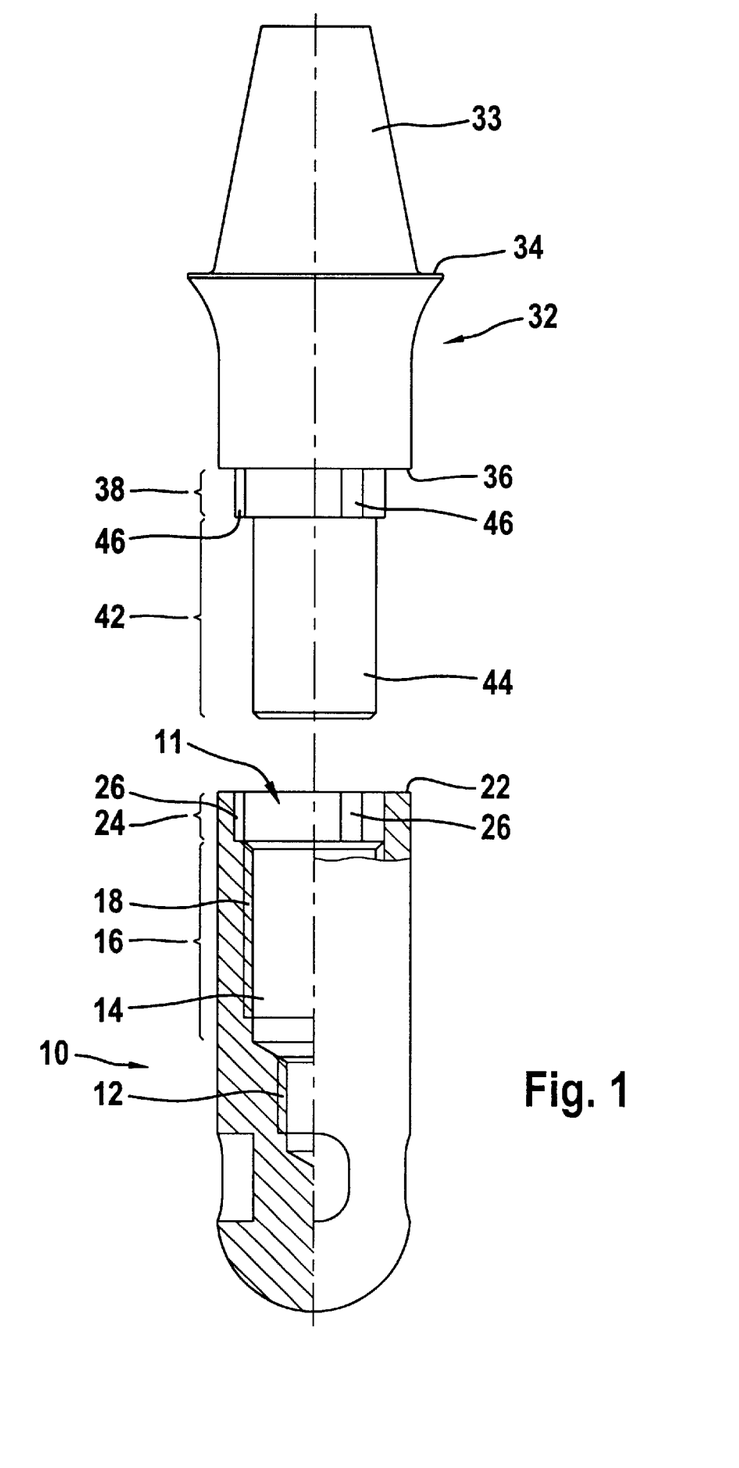
FIG. 1 shows a first exemplary embodiment of a single tooth implant of the invention in an exploded illustration, partially in a longitudinal section.
Figure 2:
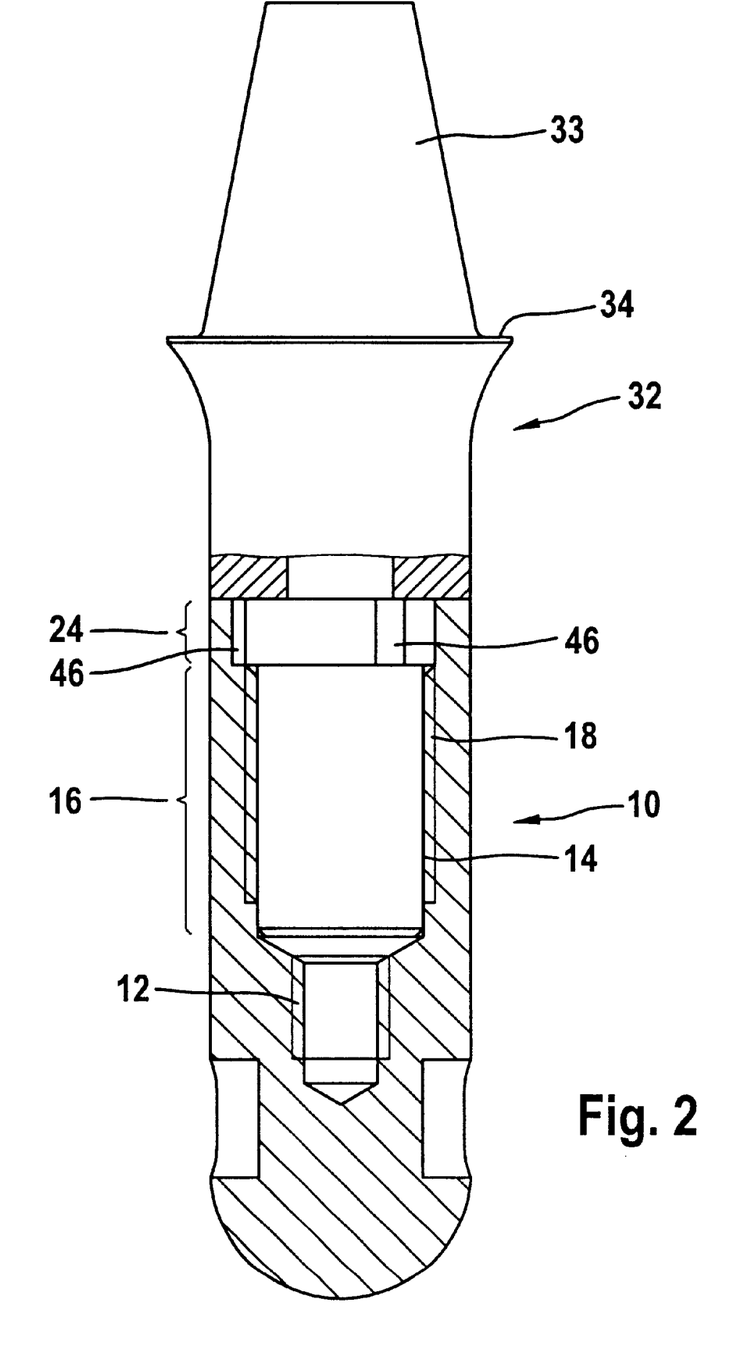
FIG. 2 shows the exemplary embodiment of FIG. 1 in its assembled condition.

As FIGS. 1 and 2 reveal, the single tooth implant given the exemplary embodiment shown therein comprises a base member 10 that is similar to that disclosed, for example, in DE 195 34 979 C1.

The base member 10, which is fashioned closed at its cervical or second end shown at the bottom in FIG. 1, comprises a blind bore opened toward its coronal or one end lying at the top in FIG. 1. An inside thread 12 having a relatively small diameter is located close to the cervical end of the blind bore, an abutment screw (not shown in the drawing of FIG. 1 and to be discussed later) can be screwed into the thread. A ring recess 14 having an enlarged diameter compared to the inside thread 12 follows the inside thread 12 of the base member in the coronal or one direction.

In a centering region 16, coronally adjoining the inside thread 12, the ring recess 14 comprises an inside thread 18. A positive lock region 24 of the ring recess 14 adjoins the centering region 16 of the ring recess 14 in coronal direction up to a coronal or end face edge 22 of the base member 10, a plurality of axial positive lock channels 26 being worked into the inside wall of the ring recess 14 therein. An annular undercut can be provided between the centering region 16 and the positive lock channels 26, this facilitating a fabrication of the positive lock channels 26 free of chip deposits.

An abutment 32 comprises a fasting head 33 for a firmly seated dental prosthesis (not shown) and is provided with an all around attachment shoulder 34 for the dental prosthesis. A shoulder 36 that can be placed onto the face edge 22 of the base member 10 and it is fashioned an all around annular shoulder is followed by a positive lock section 38 and a centering section 42 of a centering collar 44. A plurality of axially proceeding positive lock noses 46 are provided in the positive lock region 38, these corresponding in shape and arrangement if not necessarily in number to the positive lock channels 26 of the base member 10. The positive lock region 38 of the abutment 32 can comprise an annular undercut between the shoulder 36 and the positive lock noses 46, this facilitating a fabrication of the positive lock noses 46 that avoids chip deposits.

Upon insertion of the abutment 32—that is provided with an axial longitudinal bore whose inside diameter corresponds to the outside diameter of the implant post (not shown)—into the base member 10, the centering section 42 of the centering collar 44 engages into the centering region 16 of the ring recess 14, whereby, thus, the smooth cylinder generated surface of the centering region 42 is seated against the inside limitation of the inside thread 18 of the centering region 16 of the base member 10. The centering section 42 of the abutment 32 is seated with a snug fit in the centering region 16 of the base member 10, namely over its longitudinal extent. The positive lock noses 46 engage into the positive lock channels 26, whereas the shoulder 36 is seated against the face edge 22. The abutment 32 is thus joined to the base member 10 and protected against twisting. The abutment 32 can be firmly joined to the base member 10 with the implant post penetrating the abutment 32 and being screwed into the inside thread 12 of the base member 10.

Figure 3:
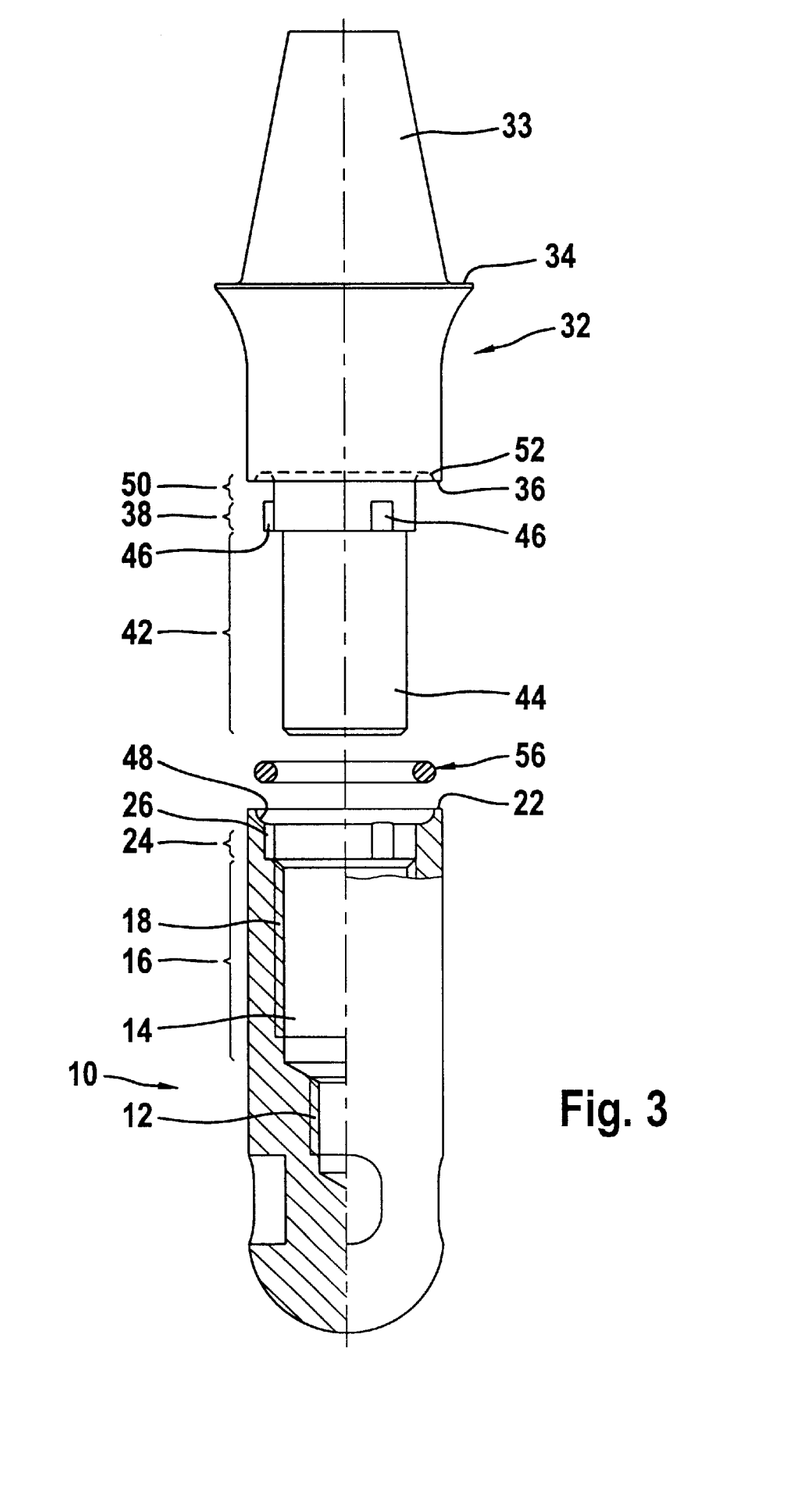
FIG. 3 shows a second exemplary embodiment of a single tooth implant of the invention in an exploded view, partially in a longitudinal section.
Figure 4:
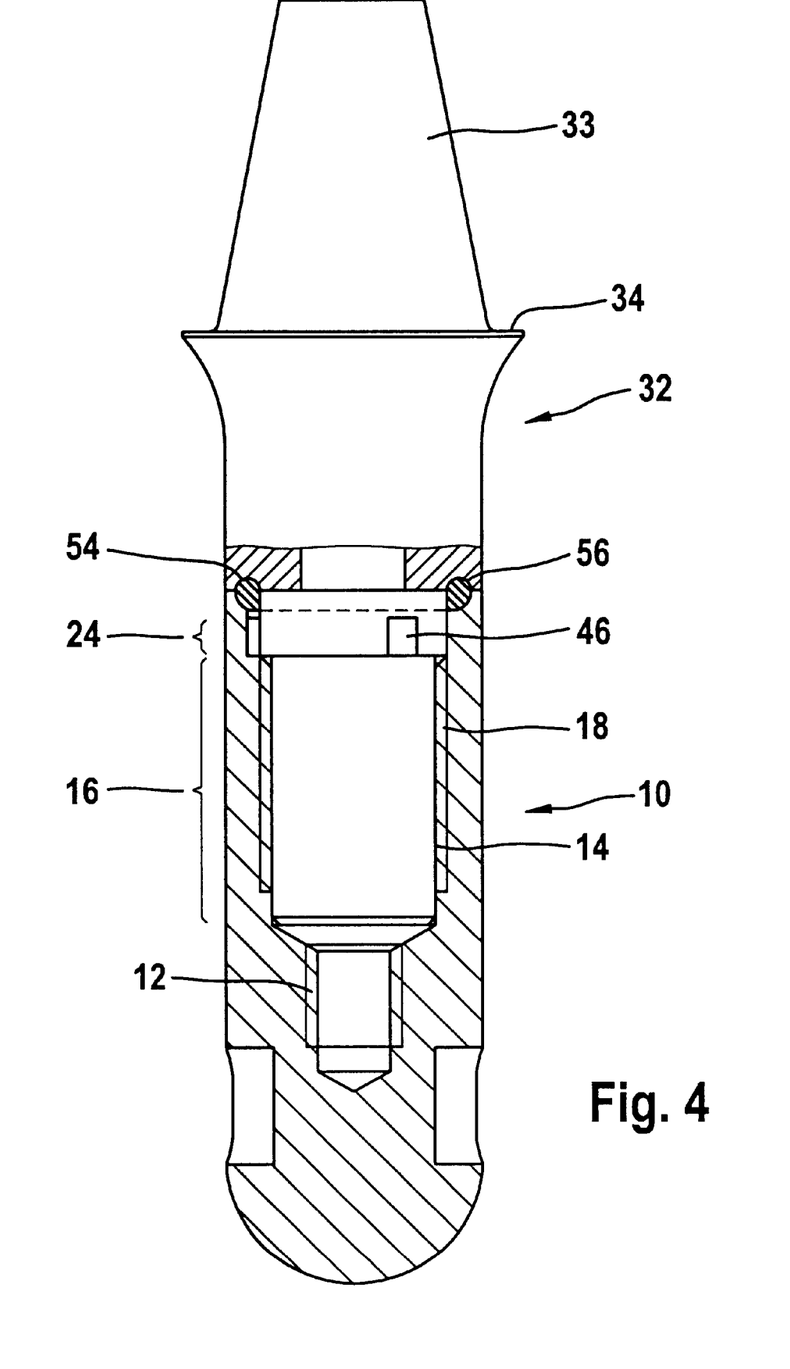
FIG. 4 shows the exemplary embodiment of FIG. 3 in its assembled condition.

Component parts that are the same and have the same effect are provided with the same reference characters in the illustration of the second exemplary embodiment of the invention in FIG. 3 and in FIG. 4. In the embodiment according to FIGS. 3 and 4, the positive lock section 38 is provided at a cervical distance or a short distance away from the shoulder 36. The positive lock section 38 of the abutment 32 comprises an annular undercut between the shoulder 36 and the positive lock noses, this facilitating the fabrication of the positive lock nose 46 avoiding chip deposits.

Proceeding from the coronal face edge 22 of the base member 10, a concave base member seal surface 48 extends in the direction onto the cylinder surface of the positive lock region 24 lying between the positive lock channels 26 of the base member, said seal surface 48 being fashioned partially toroidally such that it has the shape of a quarter-circle surface in the cross-section through the longitudinal center axis of the base member.

A cylindrical boundary surface 50 whose outside diameter corresponds to that of the positive lock section 48 of the centering collar 44 outside the positive lock noses 46 extends between the positive lock section 38 of the abutment 32 and the shoulder 36. An abutment seal surface 52, which has a semi-circular shape in the cross-section through the longitudinal center axis of the abutment 32, adjoins the boundary surface 50 in the seating surface of the shoulder 36 perpendicular to the longitudinal center axis of the abutment 32, and the abutment seal surface 52 is formed by a flat, circular shell-shaped annular channel.

When the base member 10 and the abutment 32 a rejoined, the base member seal surface 42 and the abutment seal surface 52 form an essentially annular seal chamber 54 into which an O-ring 56 of comparatively soft, elastic, compressible materials such as silicone or the like can be placed. When the base member 10 and the abutment 32 are pressed together with the abutment screw (not shown), which is screwed into the inside thread 12 of the base member 10, a compression of the seal ring 56 ensues in such a way that the inside of the implant is reliably sealed against external influences and, thus, against bacterial attack, etc.

Figure 5:
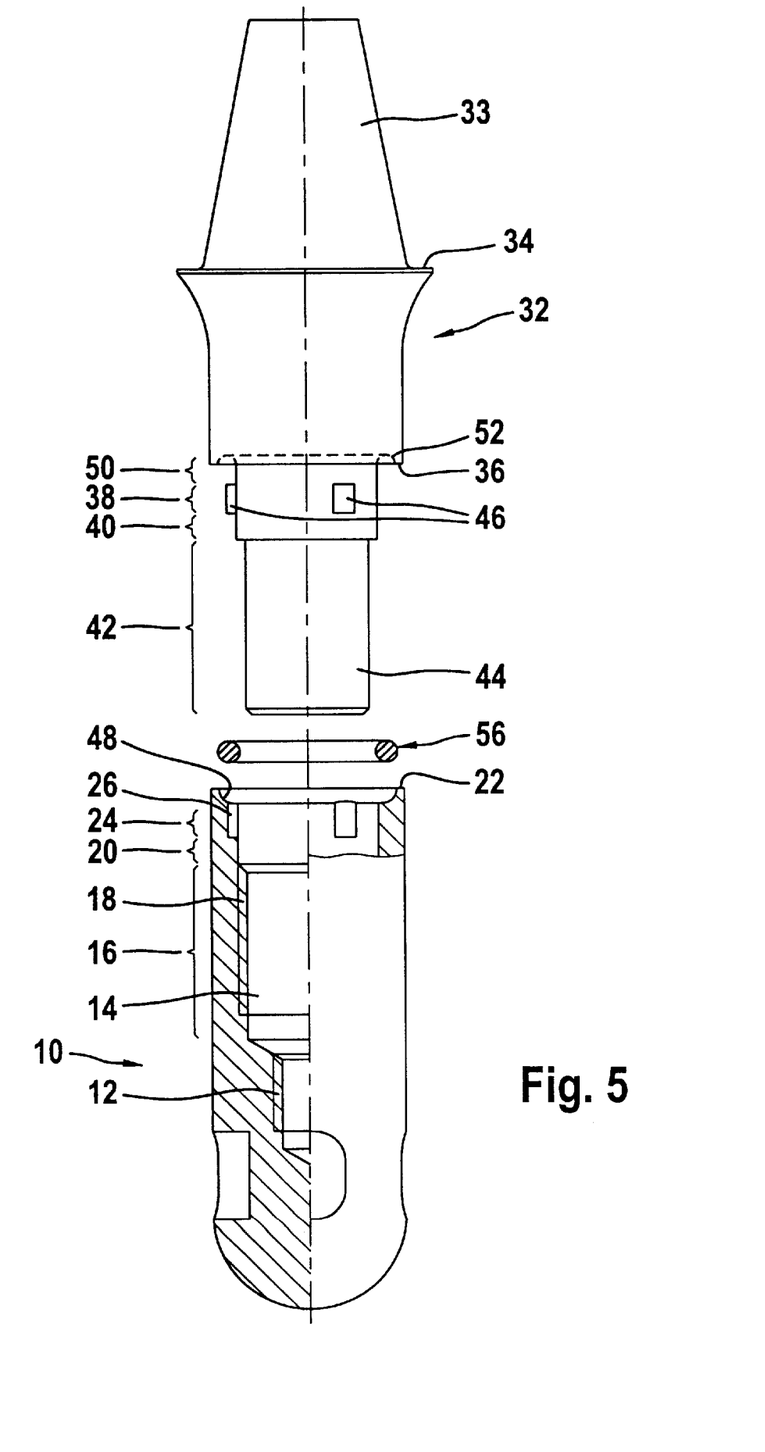
FIG. 5 shows a third exemplary embodiment of a single tooth implant of the invention in an exploded view, partially in longitudinal section.
Figure 6:
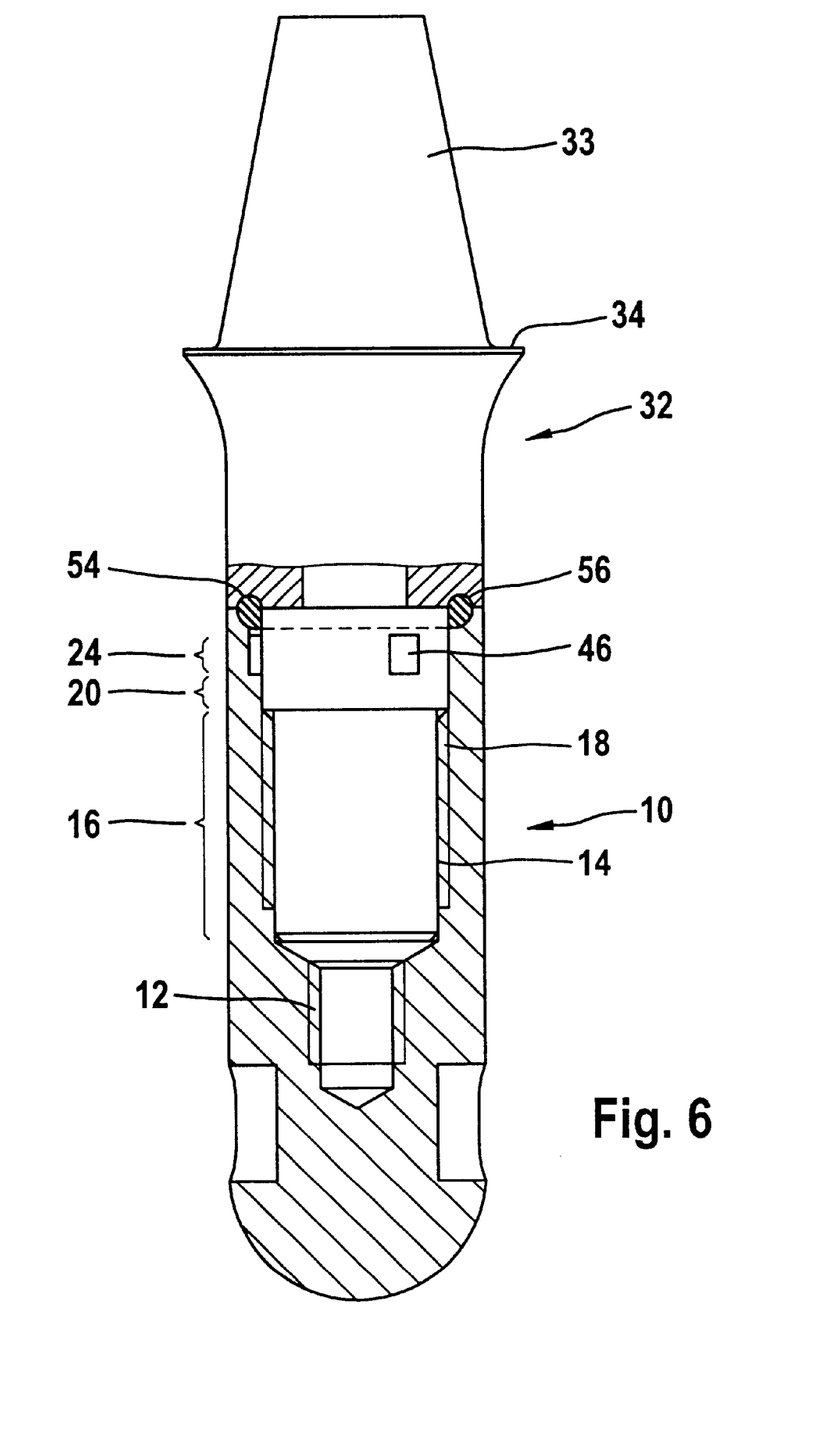
FIG. 6 shows the exemplary embodiment of FIG. 5 in its assembled condition.

The third exemplary embodiment of the invention shown in FIGS. 5 and 6 is similar to the exemplary embodiment of FIGS. 3 and 4 insofar as it comprises a seal ring between abutment and base member that, as described above, effects a biological seal. However, it differs in terms of the structure of the base member or, respectively, of the abutment. Identical elements and elements having the same effect are again provided with the same reference characters in FIGS. 5 and 6 as in the preceding Figs. The description of the preceding exemplary embodiments is referenced in view of coinciding features.

In this third exemplary embodiment, which is shown in FIGS. 5 and 6, the ring recess 14 again comprises a center of the ring region 16 coronally adjoining the inside thread 12 and comprises an inside thread 18. Differing from the preceding exemplary embodiments, however, a guide region 20 adjoins the centering region 16 of the ring recess 14 in coronal direction, the ring recess 14 exhibiting an enlarged diameter here compared to the centering region 16 having a smooth, hollow-cylindrical inside wall in said guide region 20. A positive lock region 24 of the ring recess 14 in which a plurality of axial positive lock channels 26 are worked into the inside wall of the ring recess 14 extends from the guide region 20 up to a coronal face edge 22 of the base member 10. An annular undercut can be provided between the guide region 20 and the positive lock channels 26, this facilitating a fabrication of the positive lock channels 26 that is free of chip deposits.

At a cervical distance or space from the shoulder 36 that can be put in place on the face edge 22 of the base member and that is fashioned as an all around annular shoulder, the abutment 32 comprises a positive lock section 38, a guide section 40 and a centering section 42 of a centering collar or shaft 44. A plurality of axially proceeding positive lock noses 46 are again provide in the positive lock region 38, these corresponding in shape and arrangement if not necessarily in number to the positive lock channels 26 of the base member 10. The positive lock region 38 of the abutment 32 again comprises an annular undercut between the shoulder 36 and the positive lock noses 46, this facilitating the fabrication of the positive lock noses 46 while avoiding chip deposits.

Upon insertion of the abutment 32, which is again provided with an axial longitudinal bore whose inside diameter corresponds to the outside diameter of the implant post (not shown), into the base member 10, the centering section 42 of the centering collar 44 engages into the centering region 16 of the ring recess 14, whereby, thus, the smooth cylindrical generated surface of the centering region 42 comes to be seated against the inner limitation of the inside thread 18 of the centering region 16 of the base member 10. The guide section 40 of the abutment 32 is seated with a snug fit in the guide region 20 of the base member 10. The positive lock noses 46 engage into the positive lock channels 26, whereas the shoulder 36 comes to lie against the face edge 22. The abutment 32 is thus joined to the base member 10 and is protected against twisting. The abutment 32 can be firmly joined to the base member 10 with the abutment screw penetrating the abutment 32 and being screwed into the inside thread 12 of the base member 10.

As in the second exemplary embodiment, a concave base member seal surface 48 is partially toroidally fashioned in the base member, and an abutment seal surface 52 again formed by a flat, circular shell-shaped annular channel, adjoins a boundary surface 50 of the abutment 32, whereby the base member seal surface and the abutment seal surface 52, in their assembled condition, form an essentially annular seal chamber 54 into which an O-ring 56—as described above can be placed, exactly as was the case given the exemplary embodiment according to FIGS. 3 and 4. When the base member 10 and the abutment 32 are pressed together with the implant post, a compression of the seal ring 56 ensues exactly as in the exemplary embodiment according to FIGS. 3 and 4 in such a way that the inside of the implant is dependably sealed against external influences and, thus, against bacterial attack as well, etc.

Both individually as well as in arbitrary combination, the features of the invention disclosed in the above description, in the claims and in the drawings can be critical for realizing the various embodiments of the invention.

What is claimed is:

1. An enossal single-tooth implant for a tight-fitting dental prosthesis having an abutment and an essentially cylindrical base member insertable into a bore introduced into a jawbone, said base member having a blind bore open toward one end of the base member and extending toward a closed end of the base member, said abutment being attachable to a face edge of the base member and being secured against twisting, said abutment having a centering collar at a first end insertable into a hollow cylindrical ring recess provided adjacent the one end of the base member, and a fastening head for the dental prosthesis separated from the centering collar by a shoulder receivable on the end face of the base member, said abutment having a through center bore for the acceptance of an abutment screw that penetrates through the abutment and can be introduced into the blind bore of the base member, said base member having a positive lock region in the ring recess comprising at least one base member positive lock element acting in a circumferential direction and the centering collar having a positive lock section of at least one abutment positive lock element complementary to the base member positive lock element, said positive lock region and positive lock section coacting to prevent twisting between the abutment and base member, the ring recess having a centering region arranged inward toward the closed end from the positive lock region, a circumferential guide surface of the positive lock region lying closest to the longitudinal center axis of the ring recess lies on a cylinder surface whose diameter is larger than the diameter of the centering region, the abutment positive lock element being provided spaced toward the first end from the shoulder on the cylindrical outside wall of the centering collar, the circumferential surface of the positive lock section lying closest to the longitudinal center axis of the centering collar lies on a cylindrical surface, whose diameter essentially corresponds to that of the cylindrical surface on which the circumferential guide surface of the positive lock region lying closest to the longitudinal center axis of the ring recess, a cylindrical centering section being arranged between the positive lock section and the first end of the abutment, the outside diameter of the centering section essentially coinciding with the inside diameter of the centering region of the base member, the improvements comprising the positive lock region being arranged inward of the end face of the base member, the end face of the base member merging with an annular base member sealing surface, which is fashioned concavely in a radial cross-section into a circumferential guide surface of the positive lock region, the positive lock section being arranged spaced from the shoulder toward the first end, the abutment having a cylindrical boundary surface between the positive lock section and said shoulder, the diameter of said boundary surface corresponding to the diameter of the centering collar and the cylindrical positive lock section outside of the abutment positive lock element, the shoulder extending from the boundary surface comprising an shell-shaped annular channel that forms a partially toroidal abutment sealing surface, the base member sealing surface and the abutment sealing surface interacting with one another to form an essentially toroidal seal chamber for the at least approximately complete acceptance of a seal ring and the seal ring composed essentially of elastically deformable material being received in said seal chamber.

2. An enossal single-tooth implant according to claim 1, wherein the sealing surface of the base member and the sealing surface of the abutment are respectively partially toroidally fashioned.

3. An enossal single-tooth implant according to claim 1, wherein the centering region is immediately adjacent a positive lock region and extends toward the close end of a base member and the centering section is immediately adjacent the positive lock section of the crown member.

4. An enossal single-tooth implant according to claim 1, wherein the centering region is provided with an inside thread over at least a part of its longitudinal extent.

5. An enossal single-tooth implant according to claim 4, wherein the centering region is provided with an inside thread only in a part of the longitudinal extent immediately adjacent the positive lock region.

6. An enossal single-tooth implant according to claim 5, wherein the inside thread extends over at least 50% of the axial longitudinal extent of the centering region.

7. An enossal single-tooth implant according to claim 6, wherein the inside thread extends over about two-thirds of the axial longitudinal extent of the centering region.

8. An enossal single-tooth implant according to claim 1, which includes a guide region of the ring recess having an essentially smooth circumferential wall adjacent the positive lock region, the diameter of said smooth circumferential wall corresponding to the cylindrical surface of said circumferential guide surface of the positive lock region closest to the longitudinal center axis of the ring recess, that the centering region of the ring recess adjoining the guide region is inward toward the closed end of the base member, said centering region having a reduced diameter compared to the guide region, the cylindrical guide section of the abutment being immediately adjacent the positive lock section, the outside diameter of said cylindrical guide section essentially corresponding to the inside diameter of the guide region, and the centering section of the abutment extending from said guide section toward said first end.

9. An enossal single-tooth implant according to claim 8, wherein the positive lock region comprises an annular undercut between the base member positive lock element and the guide region.

10. An enossal single-tooth implant according to claim 1, wherein the seal ring is an O-ring.

11. An enossal single-tooth implant according to claim 1, wherein the seal ring is composed of a silicone plastic.

12. An enossal single-tooth implant according to claim 1, wherein the seal ring is selected from a group of materials comprising bacteriostatical material and bacteriocidal material.

13. An enossal single-tooth implant according to claim 1, wherein the blind bore has inside threads adjacent the closed end.

14. An enossal single-tooth implant according to claim 13, wherein an abutment screw can be screwed into the inside threads to mount the abutment on said base member.

15. An enossal single-tooth implant according to claim 1, wherein the positive lock section of the abutment comprises an annular undercut between the shoulder and the positive lock element of the abutment.

16. An enossal single-tooth implant according to claim 1, wherein the axial depth of the annular channel is in a range of 0.2 mm to 0.4 mm.

17. An enossal single-tooth implant according to claim 1, wherein the radial width of the annular channel is in a range of 0.2 mm to 0.5 mm.

18. An enossal single-tooth implant according to claim 1, wherein the axial distance of the positive lock region from the end face of the base member is in a range of 0.2 mm to 0.5 mm.

19. An enossal single-tooth implant according to claim 1, wherein the axial thickness of the seal ring in an unstressed condition is in a range of 0.2 mm to 0.6 mm.

20. An enossal single-tooth implant according to claim 1, wherein the outside diameter of the base member in the region of the end face is in a range of 2.0 mm to 7.0 mm.

* * * * *